United States Patent [19]

Urquhart et al.

[11] Patent Number: 4,515,585
[45] Date of Patent: * May 7, 1985

[54] SYSTEM FOR PARENTERAL ADMINISTRATION OF AGENT

[75] Inventors: John Urquhart, Palo Alto; Felix Theeuwes, Los Altos, both of Calif.

[73] Assignee: ALZA Corporation, Palo Alto, Calif.

[*] Notice: The portion of the term of this patent subsequent to Feb. 21, 2001 has been disclaimed.

[21] Appl. No.: 547,427

[22] Filed: Oct. 31, 1983

Related U.S. Application Data

[63] Continuation of Ser. No. 381,402, May 24, 1982, Pat. No. 4,432,754.

[51] Int. Cl.³ ............................................. A61M 5/14
[52] U.S. Cl. ...................................................... 604/85
[58] Field of Search ............................. 604/56, 80–86

[56] References Cited

U.S. PATENT DOCUMENTS

| | | | |
|---|---|---|---|
| 1,654,745 | 1/1928 | Miller | 604/83 |
| 2,254,994 | 9/1941 | Butland | 604/80 |
| 2,849,256 | 8/1958 | Kowal | 299/84 |
| 2,954,028 | 9/1960 | Smith | 604/80 |
| 3,305,446 | 2/1967 | Bechtol | 167/72 |
| 3,756,237 | 9/1973 | Chittenden et al. | 128/227 |
| 3,760,984 | 9/1973 | Theeuwes | 222/95 |
| 3,797,494 | 3/1974 | Zaffaroni | 128/268 |
| 3,845,770 | 11/1974 | Theeuwes et al. | 128/260 |
| 3,854,480 | 12/1974 | Zaffaroni | 128/260 |
| 3,921,636 | 11/1975 | Zaffaroni | 128/260 |
| 3,941,126 | 3/1976 | Dietrich et al. | 604/83 X |
| 3,948,254 | 4/1976 | Zaffaroni | 128/127 |
| 3,993,066 | 11/1976 | Virag | 128/214 |
| 3,993,072 | 11/1976 | Zaffaroni | 128/260 |
| 3,993,073 | 11/1976 | Zaffaroni | 128/260 |
| 3,995,631 | 12/1976 | Higuchi et al. | 128/260 |
| 4,177,256 | 12/1979 | Michaels et al. | 424/22 |
| 4,203,439 | 5/1980 | Theeuwes | 128/260 |
| 4,217,894 | 8/1980 | Franetzki | 604/84 X |
| 4,219,022 | 8/1980 | Genese | 128/214 |
| 4,233,973 | 11/1980 | Shukla | 604/84 |
| 4,256,104 | 3/1981 | Muetterties et al. | 128/214 |
| 4,256,105 | 3/1981 | Leahey et al. | 128/214 |
| 4,320,759 | 3/1982 | Theeuwes | 128/260 |
| 4,325,368 | 4/1982 | Kaemmerer | 128/260 |

FOREIGN PATENT DOCUMENTS 497181 11/1970 Switzerland .

OTHER PUBLICATIONS

Surgery, vol. 70, pp. 674–677, 1971.
Brit. J. Anaesth, vol. 43, pp. 681–686, 1971.
Am. J. of I.V. Therapy, pp. 27–31, Jan.–Dec. 1975.
Am J. Hosp. Pharm., vol. 32, pp. 892–897, 1975.

*Primary Examiner*—Dalton L. Truluck
*Attorney, Agent, or Firm*—Paul L. Sabatine; Edward L. Mandell; Steven F. Stone

[57] ABSTRACT

A parenteral delivery system is disclosed for administering a beneficial agent to a recipient. The system comprises (a) a primary container of a medical fluid; (b) a primary drip chamber in fluid communication with the primary container; (c) a primary formulation chamber in fluid communication with the primary drip chamber and housing an agent dispensing device or a beneficial agent; (d) a secondary container of a medical fluid; (e) a secondary drip chamber in fluid communication with the secondary container; (f) a secondary formulation chamber in fluid communication with the secondary drip chamber and housing an agent dispensing device or a beneficial agent; and (g) a common tubing in communication with the primary formulation chamber and the secondary formulation chamber for communicating the system with the recipient.

7 Claims, 13 Drawing Figures

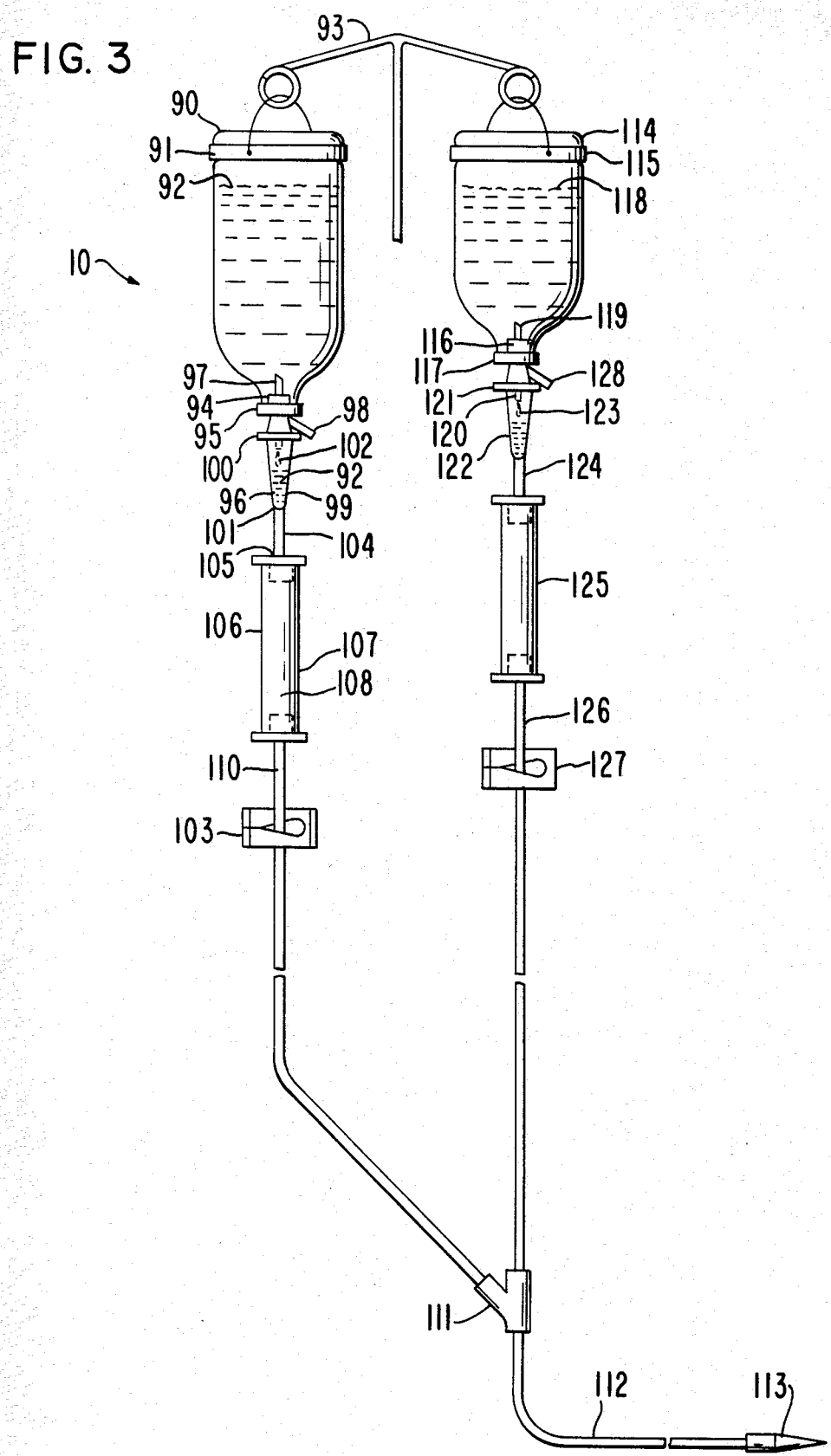

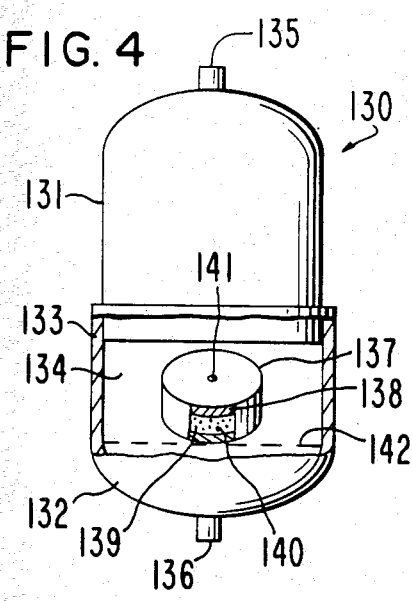
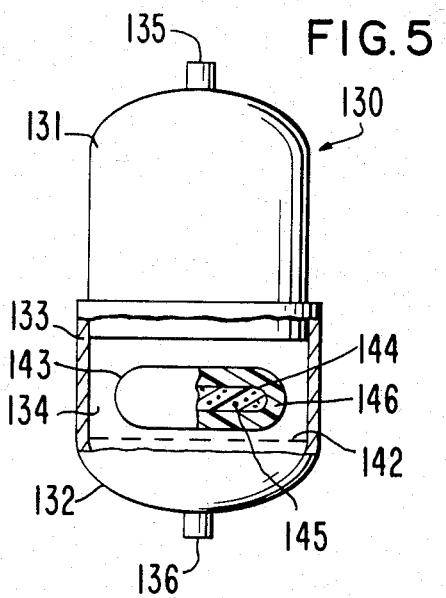
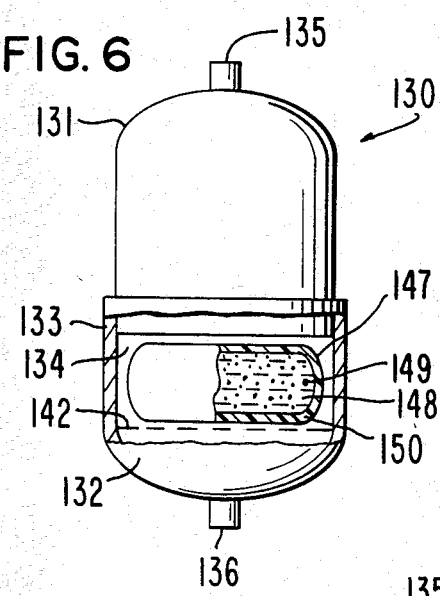
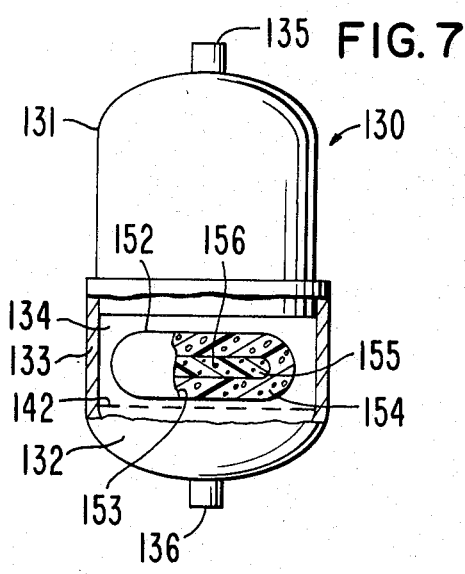
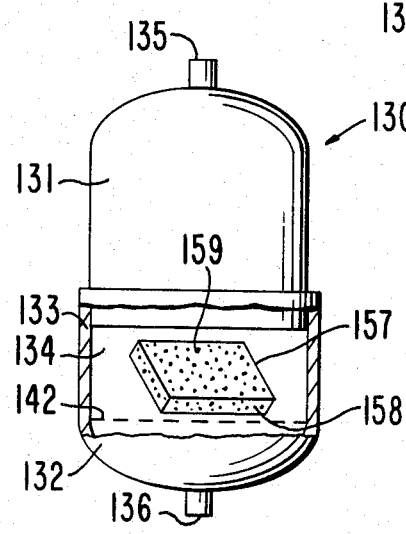

SYSTEM FOR PARENTERAL ADMINISTRATION OF AGENT

CROSS-REFERENCE TO COPENDING APPLICATIONS

This application is copending with U.S. Pat. Appln. Ser. No. 325,204 filed on Nov. 27, 1981, now U.S. Pat. No. 4,424,056, issued on Jan. 3, 1981, and U.S. Pat. Appln. Ser. No. 325,206 filed on Nov. 27, 1981, and now U.S. Pat. No. 4,432,756, issued on Feb. 21, 1984. This application is a continuation of U.S. patent application Ser. No. 06/381,402 filed on May 24, 1982, and now U.S. Pat. No. 4,432,754, issued on Feb. 21, 1984. This application and the copending applications are assigned to the ALZA Corporation of Palo Alto, California.

FIELD OF THE INVENTION

This invention pertains to a parenteral delivery system. The system comprises a primary path comprising a formulation chamber and a secondary path comprising a formulation chamber. The formulation chamber, in both systems, contains a beneficial agent delivery system, or a beneficial agent. The invention relates also to a method of administering parenterally an agent using the parenteral delivery system.

BACKGROUND OF THE INVENTION

Parenteral drug therapy first was used in experiments over three hundred years ago. In 1656, Christopher Wren using a quill and a bladder injected intravenously opium into dogs. Six years later in 1662, Johann Daniel Major performed the first successful intravenous administration of an elusive "medical substance" for anesthetic purposes in humans. An animal suffering from a loss of blood was restored, in 1662, by an infusion of blood from another animal, and shortly thereafter in 1667, a Parisian boy was the first human to receive a blood transfusion. About 200 years later in 1832, Thomas A. Latta infused intravenously large volumes of saline solution into cholera victims, and although his efforts met with some success, serious complications arose from infections, and death was a frequent outcome. From this time until the twentieth century, intravenous administration virtually stopped because the procedures used were unsterile and the blood was unmatched, which conditions led to fatal results. In 1920 Karl Landsteiner established the major blood groups, and around 1923, with the discovery and elimination of pyrogens, coupled with the use of sterile techniques, the administration of parenteral fluids intravenously became safer and more frequent. Today the parenteral administration of sterile fluids is an established clinical practice, and this practice is used extensively as an integral part of the daily treatment of medical and surgical patients.

The fluids administered parenterally, usually intravenously, include aqueous solutions of dextrose, sodium chloride, and various other electrolytes. Blood and blood substitutes are always administered intravenously. Generally, the fluids are administered from a container that is suspended above the patient, with the fluid flowing from the container through an administration set and thence to a cannula or a hypodermic needle placed in a blood vessel, usually a vein. For intraperitoneal administration of fluids, the administration set is connected to a cannula traversing the abdominal wall of the patient.

The adimnistration of fluids parenterally is a valuable and important component of patient care. The use of parenteral fluids moreover has in recent years expanded beyond its original role of fluid and electrolyte replacement to include serving as a vehicle for the parenteral administration of various beneficial agents, including drugs. Notably, the expanded use has occurred where it is desirable to administer a single drug by infusion via the intravenous, intra-arterial, intraperitoneal or subcutaneous routes; however, the expanded use has not occurred where it is desirable to administer more than one drug, mainly because the prior art has not provided a delivery system for this purpose, and because of the potential incompatibility of some drugs. Presently, a single drug is administered, for example, intravenously by one of the following procedures: temporarily halting the flow of medical fluid and intravenously administering a solution of drug to the patient through an injection port in the administration set, followed by resumption of medical fluid into the patient; a drug is added to the fluid in the container, or into a volume control chamber in series with the administration set, and then carried by the flow of fluid into a patient; a drug is introduced into a piggyback container, which is subsequently connected through a connector, in tributary fashion, to the primary administration set through which fluid is administered to the patient; or a drug is administered by a pump which, by one of various recognized pumping actions, establishes flow and this determines the flow of fluid containing the drug into a flow path entering the patient, for example, an indwelling venous catheter.

While the prior art has provided delivery systems and procedures for administering a single agent to a recipient, the prior art heretobefore has not provided a parenteral delivery system that can be used clinically for administering parenterally (a) a single agent according to a preselected program comprising continuous administration, repeated administration, administration at specific intervals, or as needed administration; and, which parenteral delivery system also can be used clinically for administering parenterally (b) more than one agent according to a preselected program comprising concurrent administration, successive administration, or alternating agent administration.

It will also be apparent in view of the above that a pressing need exists for a parenteral delivery system that is both dependable and practicable for delivering more than one agent while simultaneously lessening the possibility of agent incompatibility that can occur when more than one agent is administered to a recipient at a controlled rate and in a beneficially effective amount over time.

DISCLOSURE OF THE INVENTION

Accordingly, it is a principle object of this invention to provide both a novel and useful parenteral delivery system for administering a fluid and at least one beneficial agent at controlled rate and according to a chosen therapeutic regimen of administration and in an improved manner for optimizing the care of a warm-blooded animal whose prognosis benefits from parenteral administration.

Another object of the invention is to provide a parenteral delivery system comprising a primary fluid path comprising a formulation chamber, and a secondary fluid path comprising a formulation chamber for forming in situ an agent solution for administering to animals or humans.

Another object of the invention is to provide a parenteral delivery system comprising (1) a primary fluid path comprising a formulation chamber containing (a) an agent delivery device for delivering an agent into a medical fluid that flows into the chamber, or (b) a beneficial agent; and (2) a secondary fluid path comprising a formulation chamber containing (a) an agent delivery device for delivering an agent into a medical fluid that flows into the chamber, or (b) a beneficial agent, which agent in either (a) or (b) forms in situ an agent solution for administering to an animal or human.

Another object of this invention is to provide a parenteral delivery system comprising (1) a primary fluid path having a formulation chamber, and (2) a secondary fluid path having a formulation chamber, and which system can be used for improved health care by making available to the practitioner (a) a mechanism for administering a fluid containing an agent via the primary path, (b) a mechanism for administering a fluid containing an agent via the secondary path, and (c) a mechanism for administering a fluid containing an agent via the primary and secondary path at a plurality of different delivery programs by selecting and regulating the delivery patterns of both paths to effect the desired program.

Another object of this invention is to provide a parenteral delivery system comprising a primary path and a secondary path, with each path having a means for automatically constituting an agent formulation in situ by dissolving a given amount of agent in a given volume of fluid that can be administered from either path, at any selected time, including intermittent intravenous therapy.

Another object of this invention is to provide a parenteral delivery system that makes attainable a plurality of therapeutic programs of agent administration adapted to a specific clinical need by furnishing a delivery system that can administer a known volume of fluid containing from a trace to a saturating amount of beneficial agent that can be administered at any chosen time and at chosen delivery profiles.

Another object of this invention is to provide a parenteral delivery system that makes possible the delivery of two different beneficial agents at predetermined periods according to specific rates and duration of agent administration.

Another object of this invention is to provide a parenteral delivery system that makes available a regimen of agent administration comprising simultaneous administration of two agents, intervals of a single agent administration at a specified rate and for a specified duration alternating with intervals of a different administration at a specified rate and for a specified duration and alternating with the concurrent administration of two agents from the delivery system.

This invention concerns a parenteral delivery system for the administration of a medical fluid containing at least one beneficial agent to an animal, including, a human patient. The system comprises: (1) a primary fluid path comprising a container of a medical fluid, a drip chamber, an agent formulation chamber, and a primary tube that communicates with the formulation chamber and a common tube that leads to an infusion site in an animal; and (2) a secondary fluid path consisting of a container of a medical fluid, a drip chamber, an agent formulation chamber, and a secondary tube that communicates with the formulation chamber and the common tube that leads to the infusion site. The formulation chamber in the primary path and/or the secondary path comprises: (a) a wall surrounding a lumen and has a surface that permits communication with the medical fluid to flow into the formulation chamber; (b) a delivery device containing a beneficial agent that is released into the formulation chamber, or a beneficial agent in the formulation chamber, which agent in either instance forms an agent formulation with fluid that enters the formulation with fluid that enters the formulation chamber; and (c) an outlet surface that lets agent formulation leave the formulation chamber and enter the primary or secondary path and then into the common path for administration to a patient. The system additionally comprises a mechanism that can be used optionally for converting a continuously functioning process of agent formulation in the primary path or in the secondary path and releasing into (d) the common flow path so that agent administration into the patient occurs during quantitatively predetermined intervals according to a specified rate and duration quantitatively predetermined intervals according to a specified rate and duration of agent infusion, or (e) from the formulation chamber in the primary path or the secondary path into a regimen of agent administration to the patient characterized by intervals of agent infusion at a specified rate and specified duration alternating with intervals during which no agent reaches the infusion site from the primary or the secondary path.

BRIEF DESCRIPTION OF THE DRAWINGS

In the drawings, which are not drawn to scale, but are set forth to illustrate various embodiments of the invention, the Figures are as follows:

FIG. 3 is a view of yet another embodiment of a parenteral system provided by the invention;

FIG. 4 is an opened view of an agent formulation chamber adapted for use in the parenteral delivery system, with the chamber housing an osmotic delivery device;

FIG. 5 is an opened view of an agent formulation chamber housing an agent delivery device comprising a release rate controlling membrane surrounding a reservoir containing an active agent;

FIG. 6 is an opened view of an agent formulation chamber housing an agent delivery device comprising a release rate controlling membrane surrounding a different reservoir containing a beneficial agent;

FIG. 7 is an opened view of an agent formulation chamber comprising an agent delivery device having a microporous release rate membrane surrounding a reservoir containing a beneficial agent;

FIG. 8 is an opened view of a formulation chamber housing a delivery device comprising a matrix containing a beneficial agent;

In this specification and the drawing like parts in related Figures are identified by like numbers. The terms appearing earlier in the specification and in the description of the drawings are described hereafter in the disclosure.

MODES FOR CARRYING OUT THE INVENTION

Figure 1:
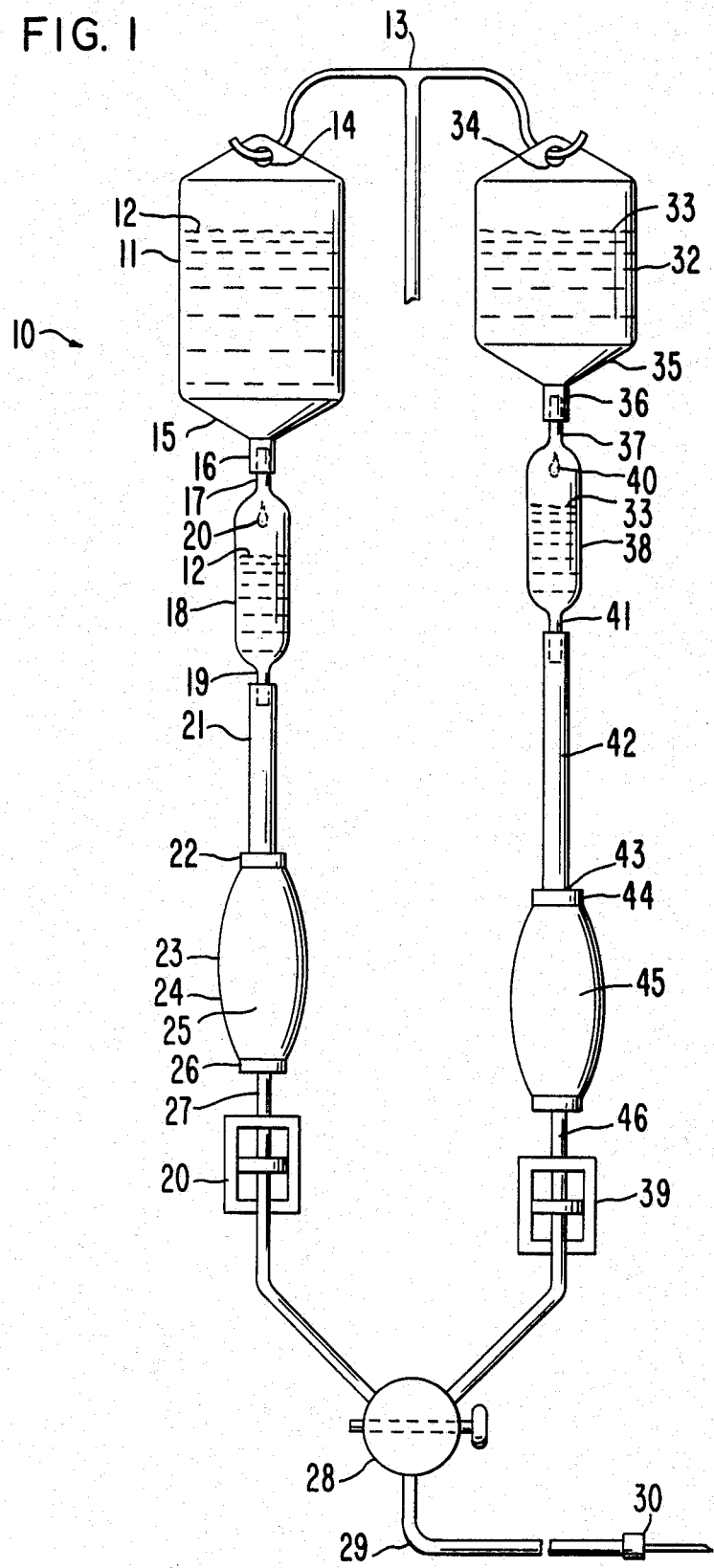
FIG. 1 is a view of a parenteral delivery system provided by the invention.

FIG. 1 represents a parenteral delivery system provided by the invention and designated by the numeral 10. System 10 comprises a primary container 11 formed of a flexible, or a semi-rigid preferably transparent plastic, formed of a non-toxic polymer such as a polyolefin, polyvinyl chloride, or the like. Primary container 11 is a large volume parenteral, LVP, container and it contains a medical fluid 12 adapted for parenteral, intravenous, or other therapy. Medical fluid 12 in container 11 will be typically a sterile solution, such as an aqueous solution of dextrose, electrolyte, or saline. Container 11, in the embodiment illustrated, is non-vented, the medical fluid is at atmospheric pressure, and the container collapses as it empties of medical fluid 12. Container 11 usually is adapted to be hung neck-down from a hanger 13 by a bib or hole that connects, or is integrally formed as part of container 11. Container 11 at its end distant from its hanging end, that is at its neck end 15 has an administration port 16 adapted for receiving a primary fluid path.

The primary path is used to deliver medical fluid 12 by parenteral therapeutic system 10 to a patient. The primary path is sterile, pyrogen-free, and disposable. The primary path comprises the components described hereinafter, and it connects with port 16 of container 11. Port 16 is a hollow connector adapted to receive end 17 of drip chamber 18. Drip chamber 18 is of conventional design, mainly a wall surrounding a fluid receiving space with an inlet end 17 and an exit end 19. Drip chamber 18 is used to trap air, and it also permits in cooperation with sliding regulator clamp 20, adjustment of the rate of flow of medical fluid 12 from container 11 as the flow proceeds dropwise. Drip chamber 18 is used for regulating the drop 20 rate for the slow but continuous introduction of glucose solution, saline solution, and the like by parenteral infusion a drop at a time.

Outlet 19 of drip chamber 18 is connected to a first section 21 of primary tube that is connected to the inlet port 22 of formulation chamber 23 for establishing fluid communication between formulation chamber 23 and drip chamber 18. Formulation chamber 23 comprises a wall 24 made of glass or a non-toxic transparent plastic that surrounds an internal space 25. Formulation chamber 23 can have any shape adapted for use in a parenteral system, and it is preferably round and its length exceeds its width. Formulation chamber 23 is designed to house a beneficial agent or an agent delivery device, both are seen in later figures, for supplying an agent to fluid that enters the formulation chamber for forming in situ an agent formulation, that is, a solution containing agent. Formulation chamber 23 optionally is equipped with a release rate controlling membrane, not shown in FIG. 1, for example a microporous membrane or the like, that governs the rate of release of agent solution from chamber 23. A release rate controlling membrane can rest on a sintered glass support integrally made into the chamber, optionally a membrane can be sealed adhesively to the inside wall of chamber 23, fused thereto, be supported by the wall of the chamber pinched inwardly, rest on a rim in the chamber, or it can be supported by outlet member 26 of formulation chamber 23. Outlet 26 is connected to a second section of tubing 27 that passes through regulator clamp 20 used for pinching its internal diameter to regulate fluid flow in cooperation with sight drip chamber 18. The other end of tube 27 connects to a three way valve 28 that receives common tube 29 which is suitably attached to needle assembly 30 for inserting it into a vein of a warm-blooded animal.

Parenteral system 10 further comprises a secondary fluid path, which secondary path consists of a secondary container 32 or mini-bag formed of a flexible, or a semirigid preferably transparent plastic, such as a non-toxic polyolefin, polyvinyl chloride, or the like. Secondary container 32 is a small volume parenteral, SVP, container and it contains a medical fluid 33 adapted for parenteral, intravenous or other therapeutic use. Medical fluid 33, like medical fluid 12, is a pharmaceutical vehicle for parenteral administration, that is, it is a pharmaceutical carrier for a drug that is to be administered to a recipient. Container 32, in the embodiment illustrated, is non-vented, medical fluid 33 is at atmospheric pressure, and the container collapses as it empties of medical fluid 33 Medical fluid 33 in the secondary path can be the same medical fluid, or a different medical fluid than medical fluid 12 in the primary path. Container 32 is adapted to be hung neck-down from hanger 13 by a bib or hole 34 that connects, or is integrally formed as a part of container 32. Container 32, at its end distant from its hanging end, that is, at its neck end 35, has an administration port adapted for receiving a secondary fluid path.

The secondary fluid path provided by the invention is used to deliver medical fluid 33 to which a drug is added to a patient. Correspondingly, the primary path provided by the invention is used also to deliver medical fluid 12 to which a drug is added to a patient. The drug in the primary path can be the same or different than the drug in the secondary path. The secondary path is sterile, pyrogen-free and made of disposable materials. The secondary path comprises the components described hereinafter, and it connects with port 36 of container 32. Port 36 is a hollow connector adapted to receive end 37 of drip chamber 38. Drip chamber 38 is used to trap air and it also permits, in cooperation with regulator clamp, adjustment of the rate of flow of medical fluid 33 from container 32, as the flow proceeds dropwise 40. An outlet 41 of drip chamber 38 is snugly positioned inside the first section of tubing 42, and the other end 43 of tube 42 is snugly positioned inside end 44 for establishing fluid communication with agent formulation chamber 45. Regulator clamp 39 is used for governing the flow of fluid 33 into drip chamber 38 and hence into formulation chamber 45. Formulation chamber 45 is made of materials compatible with parenteral fluid, usually of glass or a non-toxic transparent plastic such as a polycarbonate. Formulation chamber 45 can have any shape adapted for use in parenteral therapeutic system, and it is preferably round and its length exceeds its width. The end 43 of tube 42 fits into end 44 of formulation chamber 45 to form an air-tight leak-proof connection with formulation chamber 45 that houses at least one beneficial agent, or a delivery device. Formulation chamber 45 optionally is equipped with a release rate controlling membrane, not shown in FIG. 1, for example a diffusional, osmotic, or a microporous membrane that aids in governing the rate of release of agent solution from chamber 45. A segment of tube 46 conveys agent solution from chamber 45 through regulator clamp 39 to valve 28. Valve 28 can be positioned for permitting fluid flow from the primary path, or from the secondary path, or from both paths simultaneously. Regulator clamp 39 can be used alone, in cooperation with clamp 20, in cooperation with valve 28, and both clamps 20 and 39 can be used in cooperation with valve 28 for governing agent solution flow through the primary and/or the secondary path. Agent solution flowing through tube 46 enters common tube 29 to needle assembly 30 for infusion to a recipient.

In operation in one embodiment, parenteral system 10 can be used for example for delivering an agent solution from the primary or the secondary path as follows. Valve 28 in one position permits the passage of drug solution from chamber 24 to flow into common tube 29, while concomitantly stopping flow through tube 46; in an alternate second position, valve 28 stops flow of fluid in tube 27, but it allows flow in tube 46. When valve 28 is in the first position, the flow of medical fluid reaches the patient at a rate determined by the setting of regulator clamp 20 open to flow; when valve 28 is in its second position, the flow of medical fluid reaches the patient at a rate determined by the setting of flow regulator clamp 39. During the intervals of time valve 28 is in its second position, drug formulation proceeds in the presence of fluid in chamber 23 and its release continues from formulation chamber 23 into tube 27, but it cannot reach the patient, and so it accumulates in chamber 23 and tube 27. When valve 28 is switched to its first position, accumulated drug formulation solution in chamber 23 and tube 27 enters the patient, the quantity of which is governed by the following pharmacodynamic expression:

$$M_1 \int_{t_K}^{t_L} R_2(t)dt$$

wherein $M_1$ is the mass of drug accumulation in chamber 24 and is maximally equal to the volume of chamber 24 minus the saturated concentration of drug in solution; $t_K$ equals the time valve 28 is switched from position 2 to position 1; $t_L$ equals the time valve 28 can be switched from position 1 back to position 2; $R_2(t)$ is the rate at which the formulation chamber prepares drug solution during free flow of intravenous fluid. The rate at which volume flow reaches a patient when valve 28 is switched to position 1 is related to the flow regulation imposed by clamp 20 which preferably should be adjusted to allow flow to occur at a rate which insures that all accumulated agent enters the patient. While the above system and its operation were described with respect to one embodiment and a representative manually operated valve, it is to be understood other operative embodiments and valve systems are embraced by this invention. For example, electro-mechanical devices that automatically switch back and forth between positions 1 and 2 or the reverse operation at preset time intervals are within the scope of the present operation.

Figure 2:
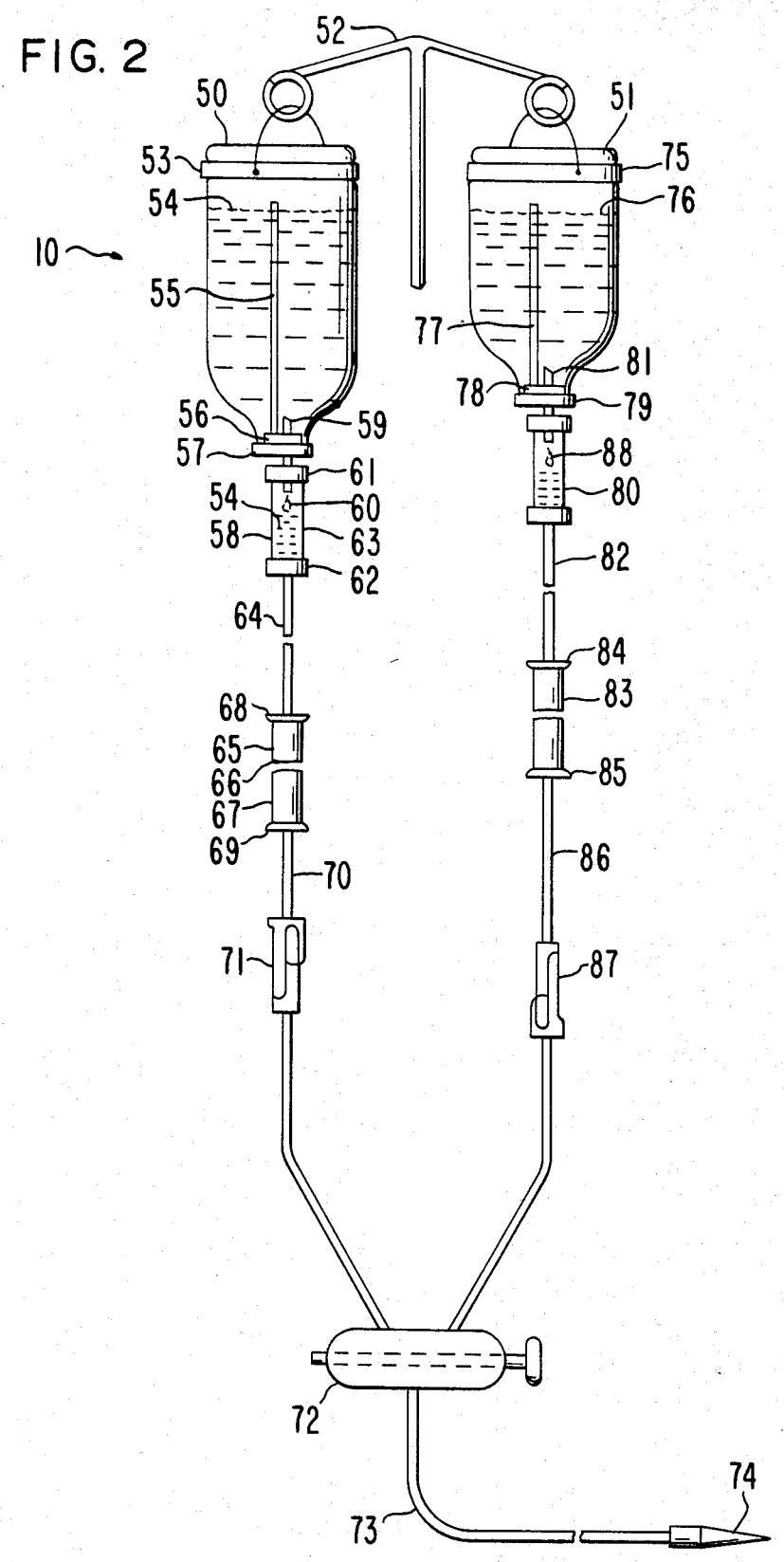
FIG. 2 is a view illustrating another embodiment of a parenteral delivery system provided by the invention.

FIG. 2 illustrates another parenteral system 10 provided by the invention. System 10 comprises a primary path 50 and a secondary path 51 supported agent fluid delivery position above a patient by looped support 52. Primary path 50 comprises in combination a container 53 that is a reservoir of a pharmaceutically acceptable liquid 54 and it has an internal venting tube 55 which allows air to enter container 53 as medical fluid leaves container 53 and is infused into a patient. Container 53 is a large volume parenteral of a sterile fluid intended for the modification and maintenance of physiological functions in a recipient. Container 53 is closed with a stopper 56 held in place by a crimped rim 57. Venting tube 55 extends through stopper 56 for admitting air into container 53. Container 53 is in fluid communication with drip chamber 58 through its hollow spiked end 59 that pierces stopper 56. Drip chamber 58, is as previously described, used for visibly counting the number of drops 60 of medical fluid 54 that passes through said drip chamber 58 over unit time. Drip chamber 58 comprises an enclosed space for holding medical fluid and it is closed at its end by a pair of caps 61 and 62 that snugly slide over tubular wall 63 to form said sterile fluid chamber. The fluid chamber is made of see-through material such as glass or clear plastic for seeing the drops. Medical fluid 54 leaves drip chamber 58 through a first section of tube 64 that carries medical fluid to formulation chamber 65. Formulation chamber 65 comprises a wall 66 that surrounds an internal space 67 and it is closed at its ends 68 and 69 by closures that fit over said chamber wall. Tube 64 enters closure 68 for establishing fluid communication between the formulation chamber and the drip chamber, and a second tube 70 that passes through a flow regulator clamp 71 transport fluid to a two-way valve 72. Fluid passes through valve 72 into common tube 73 and needle assembly 74 to a recipient.

Secondary path 51 consists of container 75 that is a means for storing a pharmaceutically acceptable liquid 76. Container 75 has an internal venting tube 77 for letting air enter container 75. Container 75 is closed by stopper 78 held in place by rim 79. Container 75 is a minicontainer, or a minibottle and it holds about 100 to 500 milliliters of liquid that is used for continuous drug transport, or for intermittent drug transport to a patient. Container 75 is connected to drip chamber 80 through hollow spike adaptor 81 for sending medical liquid from container 75 through the secondary path to a patient. Drip chamber 80 is designed for counting the number of drop 88 that pass through said drip chamber 80 over time. Medical fluid leaves the drip chamber through a first section of tubing 82 that leads to a formulation chamber 83. Agent formulation chamber 83 is as described earlier comprised of a wall formed of a fluid impermeable material that surrounds an internal space for housing a dosage unit amount of a beneficial agent, or a delivery device. Chamber 83 has a known volume and preferably a volumetric scale thereon for indicating the volume of fluid in said chamber. Chamber 83 has an end 84 adapted for receiving incoming tube 82 and an end 85 adapted for receiving outgoing tube 86. Tube 86 passes through clamp 87 and it can be used as an on-off, or a volume flow regulator for controlling fluid flow rate through the secondary path. Tube 86 conveys fluid carrying beneficial agent from chamber 83 to valve 72, and thence through fluid communicating common tube 73 to needle assembly 74, and into a living recipient.

In operation, parenteral delivery system 10 of FIG. 2 is used like parenteral delivery system 10 of FIG. 1. That is, system 10 of FIG. 2 can be used (1) for administering a preselected medical fluid containing a preselected beneficial agent by opening regulator clamp 71, closing regulator clamp 87, and positioning valve 72 to let fluid flow from tube 70 into tube 73; (2) for administering a different preselected medical fluid containing a different preselected beneficial agent by opening regulator clamp 87, closing regulator clamp 71, and positioning valve 72 to let fluid flow from tube 86 into tube 73; and (3) for administering at a selected dosing time a given volume of fluid containing a known amount of agent by (a) permitting fluid to flow through the primary or the secondary path while setting valve 72 in closed position for the primary or the secondary path, (b) permitting a known volume of fluid to enter either formulation chamber, which volume is ascertained by reading the meniscus against the volumetric scale on the chamber, (c) formulating the agent formulation in the chamber by dissolving a given amount of agent present in the chamber, or delivered by a device therein, in the known volume of fluid, which amount of agent solubility in the fluid dissolves over time, and (d) dosing a recipient with the agent solution whenever desired by position valve 72 to let it flow from the desired formulation chamber.

FIG. 3 represents a parenteral system 10 provided by the invention. Parenteral system 10 is a gravitational flow system for the administration of two medical fluids and two beneficial agents at independent, or cooperating flow rates through two distinct delivery paths, a primary path and a secondary path. The primary path 90 comprises a container 91 that contains a primary medical liquid 92 to be administered to a patient over a prolonged time and it is supported in delivery position by a hanger 93. Primary fluid supply container 91 is made from glass or transparent non-toxic plastic and it is sealed under sterile conditions. Container 91 is sealed with a rubber stopper 94 held in container 91 by annular retaining rim closure 95.

Primary container 91 is in fluid communication with a drip chamber 96. Drip chamber 96 is in fluid communication with container 91 through a hollow puncture spike 97 that passes through stopper 94 into container 91. Drip chamber 96 is a conventional, vented-type 98 drip chamber well-known to medical practice. Basically, drip chamber 96 is formed of two parts, a conical housing 99 for receiving fluid, and it is capped 100 at its inlet and terminates in an outlet orifice 101. Drip chamber 96 lets air enter the parenteral system through air inlet 98 integrally formed as part of capped inlet 100. The drip 102 rate of fluid flow from container 91 is regulated by a clamp 103 provided down stream on the primary path. A first section of medical grade tubing 104 inserted into outlet 101 establishes fluid communication between drip chamber 96 and inlet 104 of formulation chamber 106.

Agent formulation chamber 106 is sized and adapted for use in parenteral delivery system 10. Agent formulation chamber 106 is self-contained, self-primary, self-powered and amenable to low cost manufacture. The formulation chamber is light-weight, disposable, and it is made in a presently preferred embodiment of a clear, transparent material such as glass or plastic. Formulation chamber 106 comprises a wall 107 that surrounds and forms and internal space 108, and it has an inlet closure 105 that receives tube 104, and an outlet closure 109 adapted to receive tube 110. Tube 110 passes through clamp 103 designed for restricting the internal diameter of tube 110 for regulating, or stopping the flow of fluid through the primary path. Tube 110 enters a coupler 111 made as a Y-type connecting tube for receiving primary path tube 110 and a common tube 112 that leads to an injection member 113 for administering agent formulation to a patient.

Secondary path 114 comprises a container 115 that is a minicontainer or a minibottle formed of glass or plastic, suitably sealed with a rubber stopper 116 held in container 115 by closure rim 117. Container 115 is supported in delivery position by support 93 and it contains a medical fluid 118 acceptable for both parenteral including intravenous administration and as a transporting carrier for a beneficial agent. Air enters container 115 through an air inlet 128 formed integral as part of spike 119, which spike is hollow and pierces the rubber closure 116 of container 115. The other point 120 of spike 119 passes through the closure inlet 121 of drip chamber 122 for conveying medical fluid drop-like 123 from the container into the drip chamber. Drip chamber 122 is in fluid communication via a tube 124 with formulation chamber 125. Agent formulation chamber 125 is constructed like formulation chamber 106 described in the primary path, and that description is included and is applicable for chamber 125. Formulation chamber 125 is connected to a secondary tube 126, formed of a medically acceptable material, that passes through a V-clamp 127 for regulating or stopping agent formulation flow through the secondary path. Tube 126 enters couple 111 for flow into common path 112 for infusion through needle assembly 113 into a patient.

The agent in formulation chambers 106 and 125 can be in any pharmaceutical state that forms an agent formulation comprising an agent and a medical fluid that enters chambers 106 and 125, and does not require any reconstitution or admixture prior to use. An agent formulation formed in chamber 106 and 125 leaves the respective chamber through the primary or the secondary path and enters the common path for administration to an animal, including a human patient, through the administration needle. Exemplary pharmaceutically acceptable forms that can be used in either chamber 106 or 125 include solid, crystalline, microcrystalline, particle, pellet, granules, powder, tablet, spraydried, lypohilized, forms that dissolve or undergo disintegration and dissolution in the presence of a parenteral fluid including intravenous fluids, compressed forms that undergo disintegration and dissolution in the presence of a fluid such as compressed agent, compressed powders, compressed granules, friable layers of agent, and/or the like. Agent formulation chamber 106 or 125 generally will store an amount of agent for executing a prescribed therapeutic or a beneficial program. That is, an amount of agent for the preprogrammed, delivery of a therapeutically or a beneficially effective amount of the agent to produce a therapeutic or a beneficial result. Agent formulation chambers 106 and 125 generally will have a capacity of from about 10 milliliters to 250 milliliters of fluid or more, and they can house from about 5 milligrams to 20 grams of agent or more. The expression beneficial agent, as used herein, generically denotes any substance that produces a therapeutic or a beneficial result, such as a drug, a carbohydrate, an electrolyte and/or the like. The term fluid or liquid denotes a fluid, or a liquid that can be administered parenterally including intravenously, comprising pharmaceutically acceptable fluids that are also a pharmaceutically acceptable carrier for an agent, such as water, isotonic saline, Ringer's lactate, and the like. The term formulation, and the expression formulation agent as presently used herein, generically indicates the beneficial agent is formulated, mixed, added, dissolved, suspended, solubilized, formulated into a solution, carried and/or the like in or by the fluid into a physical-chemical form acceptable for parenteral including intravenous administration. The flow of medical fluid into formulation chamber 106 or 125 can be started, stopped, regulated, or interrupted by clamp 103, or 127, alone or together, that permits tube 110 or 126 to remain open, shut or to partially obstruct the passage of fluid through tube 110 or 126, and correspondingly the flow of agent solution likewise can be governed from chamber 106 or 125.

The delivery device housed in formulation chamber 106 or 125 releases an agent at a rate controlled by the device. The agent, on its release by the delivery device, is formulated in the chamber with fluid that is a pharmaceutically acceptable carrier for the agent, into a parenteral including intravenously administrable agent formulation, such as a drug solution. Devices that can be used for this purpose are those that release an agent by dissolution, diffusion or osmotic mechanisms, or by other physical-chemical mechanisms that produce an agent formulation. The amount of agent in a formulation made in situ in chamber 106 and 125 can be a trace amount to a saturated amount. The delivery devices, in one presently preferred embodiment are devices that cease releasing agent or shut themselves off in the presence of a saturated agent formulation, that is a saturated solution.

In operation, parenteral delivery system 10 as illustrated in FIG. 3 can be used by a physician, a nurse, or a practitioner in a hospital setting as follows: (1) for administering medical fluid containing a beneficial agent through the primary path by adjusting regulator clamp 103 to open and by closing regulator clamp 127 to prevent the flow of fluid in the secondary, thus assuring the flow through the primary path and into skin piercing needle 113; (2) for administering a medical fluid containing a beneficial agent through the secondary path by adjusting regulator clamp 127 to open and by closing regulator clamp 103 to prevent the flow of fluid in the primary path, thus assuring the flow through the secondary path and into skin piercing needle 113; and (3) for administering an amount of agent in a known volume of fluid from both paths by regulating fluid flow through regulator clamps 103 and 127, which fluid in both instances mixes into a common fluid at coupling 111 for its subsequent administration to a patient. The operations provided by these operations of the invention make available continuous and interrupted administration of two different agents in two different fluids through two different paths, and administration of two different agents in different fluids during the same time interval of agents administration.

The performance of a parenteral delivery system used for the purpose of the invention, also can be described mathematically in terms of the physical and chemical functionality of the primary or the secondary path of the parenteral delivery system. Generally, for a delivery path, the parenteral systems encompassed by this invention are those for which $Q_R \leq 0.1 Q_{KVO}$, wherein $Q_{KVO}$ is the flow of fluid required to maintain flow into the veins of an animal in which a flow path terminates, by needle or by catheter. This flow is referred to as the "keep vein open", rate $Q_{KVO}$, and it typically is for an adult patient about 10–20 drops per minutes, or 0.5–1.0 ml per minute. The symbol $Q_R$ is the maximum rate of fluid flow needed for the parenteral delivery system to deliver a solution at its label rate. Thus, parenteral systems for adult use require less than 0.05–0.1 ml/min to achieve label delivery rate, and show independence of delivery rate from flows at all higher flows are encompassed by this invention. Delivery systems for pediatric use will have a lower absolute limit, but still satisfy the general criterion $Q_R \leq 0.1 Q_{KVO}$.

FIG. 4 depicts a formulation chamber housing a delivery device that can be used in the primary and secondary paths of the parenteral delivery systems of FIGS. 1 to 3. The formulation chambers described in this specification are the invention disclosed and claimed by Felix Theeuwes in copending patent applications identified by attorney Ser. No. 310,047 filed on Oct. 9, 1981 and Ser. No. 312,491 filed on Oct. 19, 1981. Both of these applications are assigned to the ALZA Corporation of Palo Alto, Calif., 94304, the assignee of this patent application.

FIG. 4 depicts a formulation chamber 130 comprising a top section 131 and a bottom section 132 having a portion of its wall 133 removed for viewing its internal space 134. Chamber 130 has an inlet 135 adapted and sized for placing chamber 130 into the primary path or the secondary path of a parenteral system. Chamber 130 has an outlet 136 also adapted for placing chamber 130 in the paths and for releasing agent formulation from chamber 130. Inlet 135 and outlet 136 can receive a tube externally that slides over the inlet and the outlet, or the inlet and outlet can receive a tube internally for establishing fluid communication with the paths. The delivery device 137 illustrated in FIG. 4 is an osmotic rate-controlled solid dosage delivery form as described by patentee Felix Theeuwes and Takeru Higuchi in U.S. Pat. No. 3,845,770. The osmotic device 137 seen in opened section comprises a semipermeable wall 138, such as cellulose acylate, cellulose diacylate, cellulose triacylate, cellulose acetate, cellulose diacetate, cellulose triacetate, and the like, that surrounds and forms a compartment 139 containing an agent 140, or drug represented by dots. The agent formulation 140 exhibits an osmotic pressure gradient across wall 138 of device 137 against fluid in chamber 130. The agent formulation can comprise an agent that exhibits an osmotic pressure gradient, or the agent formulation can comprise an agent mixed with an osmotically effective solute, such as sodium chloride, potassium chloride, and the like that exhibit an osmotic pressure gradient substantially greater than the fluid in chamber 130. A passageway 141 extends through semipermeable wall 138 and communicates with compartment 139 and the exterior of device 137. In operation fluid enters chamber 130 and is imbibed through the semipermeable wall 138 of device 137 into compartment 139 in a tendency towards osmotic equilibrium at a rate determined by the permeability of the wall and the osmotic pressure gradient across the wall, thereby producing a solution containing agent 140 in compartment 139 that is dispensed through passageway 141 at a rate controlled by device 137 over a prolonged period of time. The delivery of agent solution from device 137 for homogenously blending with fluid in chamber 130 is controlled in this embodiment by device 137 and it is essentially independent of the rate of fluid flow through chamber 130. Device 137 maintains its physical and chemical integrity throughout its releasing history. In FIG. 4 the dashed lines indicate a support member 142 for holding device 137.

FIG. 5 depicts another device 143 in the formulation chamber. The formulation chamber of FIG. 5 is as previously described, see FIG. 4, and that description is incorporated herein. Device 143 is illustrated in opened section and it comprises an inner mass transfer conductor 144 illustrated as a solid core and formed of a polymeric material such as cured polydimethylsiloxane, with agent 145 dispersed therethrough. Surrounding mass transfer conductor 144 is a release rate controlling membrane 146, preferably formed of a polymeric material, such as polyurethane, polyethylene, and the like. Both conductor 144 and membrane 146 are permeable to the passage of agent 145 by diffusion, that is, agent 145 can dissolve in and diffuse through conductor 144 and membrane 146. However, the permeability of conductor 144 is greater than that of membrane 146 and membrane 146 thus acts as the rate controlling member for agent release from device 143. Device 143 maintains its physical and chemical integrity throughout the period of agent delivery. Delivery device 143 is disclosed in U.S. Pat. No. 3,845,480.

FIG. 6 illustrates a delivery device 147 for use in the formulation chamber for delivering an agent at a rate controlled by device 147 into a fluid that enters the chamber. Device 147 is seen in opened-section and it comprises a reservoir 148 formed of a liquid mass transfer conductor, such as a medical oil carrier, permeable to the passage of agent 149, such as the drug phenobarbitol. Reservoir 148 is surrounded by a wall 150 formed of a release rate controlling material permeable to the passage of agent 149, such as a polyolefin. The rate of passage of agent 149 is lower through membrane 150 than the rate of passage through conductor 148, so that agent released by wall 150 is the agent release rate controlling step for releasing agent 149 from device 147. Device 147 maintains its physical and chemical integrity throughout its release history. Delivery device 147 is disclosed in U.S. Pat. No. 3,993,073 which patent is incorporated herein by reference.

FIG. 7 illustrates another device 152 for use in the formulation chamber for delivering an agent into a medical liquid that enters the formulation chamber for forming a parenteral agent solution including an intravenously acceptable agent solution. Device 152 is seen in opened-section 153, and it comprises a wall 154 surrounding reservoir 155 containing agent 156. The reservoir is formed of a solid carrier permeable to the passage of agent, such as cured polydimethylsiloxane containing diazepam. Wall 154 is formed of a microporous polymer made by coprecipitation of a polycation and a polyanion. The release of agent 156 is controlled by device 152 which device maintains its physical and chemical integrity during the period of time it is in the formulation chamber. Device 152 is disclosed in U.S. Pat. No. 3,993,072 which patent is incorporated herein by reference.

FIG. 8 is a view of a device in the formulation chamber for delivering an agent into a medical fluid that enters the formulation chamber for forming in situ a parenterally or an intravenously acceptable agent formulation solution. Device 157 comprises a maxtrix 158 containing agent 159 distributed therein. Matrix 158 is formed of a polymeric material that is non-erodible and it is permeable to the passage of agent by diffusion for releasing it at a controlled rate over time. Matrix 158 can be formed also of a polymer that undergoes relaxation and thusly releases agent 159 over time. The matrix can possess any shape such as rod, disc and the like that easily fits into the formulation chamber. The polymers useful for forming the device include polyolefins such as polyethylene containing an agent such as a muscle relaxant and the like. Materials useful for manufacturing the device are disclosed in U.S. Pat. No. 3,921,636.

Figure 9:
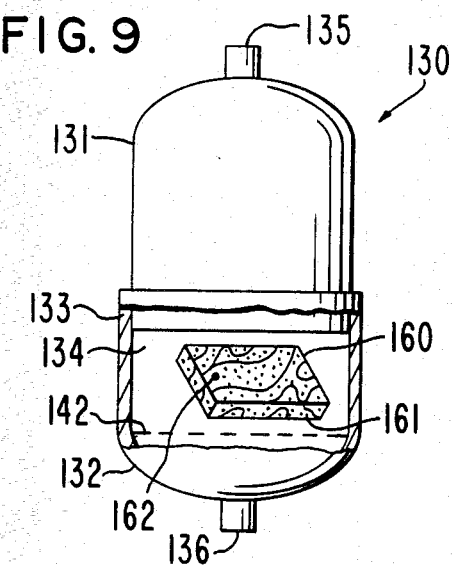
FIG. 9 is an opened view of an agent formulation chamber housing a delivery device comprising a microporous matrix containing an agent.

FIG. 9 is a view of the formulation chamber housing a different delivery device 160 for delivering a beneficial agent into a fluid that enters the formulation chamber. Device 160 is formed of a microporous polymeric matrix 161 containing beneficial agent 162 distributed therethrough. Matrix 161 is formed of a non-toxic, inert polymer, that is non-erodible and it has a plurality of micropores for releasing agent 162 at a controlled rate to a medical fluid entering the formulation chamber. Microporous materials useful for the present purpose are disclosed in U.S. Pat. Nos. 3,797,494 and 3,948,254.

Figure 10:
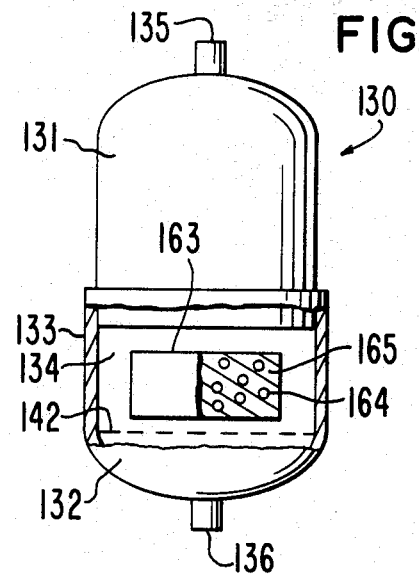
FIG. 10 is an opened view of an agent formulation chamber housing a delivery device comprising depots of agent.

FIG. 10 illustrates the formulation chamber housing another delivery device 163 for delivering a beneficial agent into a medical fluid that enters the formulation chamber. Device 163 is seen in opened section and it comprises depots 164 of medication solute dispersed in and surrounded substantially individually by a polymer wall 165 that is permeable to the passage of fluid that enters the formulation chamber and impermeable to the passage of medication solute. Medication solute is released at a controlled rate by fluid being imbibed through the polymer into the depots to dissolve the solute in the depots and generate a hydrostatic pressure in the depots. The pressure is applied against the wall of the depots thereby forming apertures that release the medication at a controlled rate over time. Device 163 is formed of a polymer that is non-erodible, and device 163 can be shaped as a matrix, rod, a disc, or of like shape. Procedures and materials useful for manufacturing the delivery system are described in U.S. Pat. No. 4,177,256.

Figure 11:
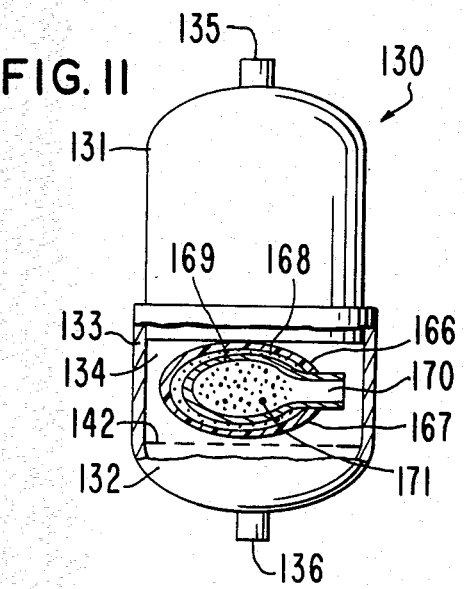
FIG. 11 is an opened view of an agent formulation chamber containing a delivery device comprising a housing and a driving member surrounding a flexible container containing a beneficial agent.

FIG. 11 illustrates a device 166 useful for delivering a drug into a medically acceptable fluid passing through the formulation chamber. Device 166 is seen in opened view and it comprises an exterior wall 167 formed of a semipermeable polymer permeable to fluid and substantially impermeable to the passage of drug and solutes. A layer 168 of an osmotically effective solute, for example sodium chloride, is deposited on the inner surface of wall 167. Solute layer 168 surrounds an inner container 169 formed of a flexible material that is impermeable to solute and drug. Container 169 has a passageway 170 for delivering drug 171 into a medical fluid present in the formulation chamber. Device 166 dispenses drug by fluid permeating from the chamber through wall 167 to continuously dissolve solute layer 168 in a tendency towards osmotic equilibrium, thereby continuously increasing the volume between wall 167 and container 169. This increase causes container 169 to continuously collapse and dispense drug 171 from device 166 at a controlled rate through passageway 170 to fluid passing through the formulation chamber. Osmotically powered agent dispensing devices are disclosed in U.S. Pat. Nos. 3,760,984 and 3,995,631.

The delivery devices described in FIGS. 4 through 11 can contain various amounts of agents, for example, from about 100 nanograms to 20 grams, or more. The devices can release an agent at a rate of 10 nanograms per hour up to 3 grams per hour, or more, into a formulation chamber for forming an agent solution with medical fluid that enters the formulation chamber. The formulation chamber optionally can be considered as a cartridge, since they can be used in the primary path or the secondary path once, or replaced many times. That is, the cartridge can be removed after all the agent is delivered, or the cartridge can be replaced repeatedly each time after the device has delivered its agent. Thus, the mode and manner of the invention can lead to continuous or intermediate therapy, in addition to the operations described in FIGS. 1 through 3.

Figure 12:
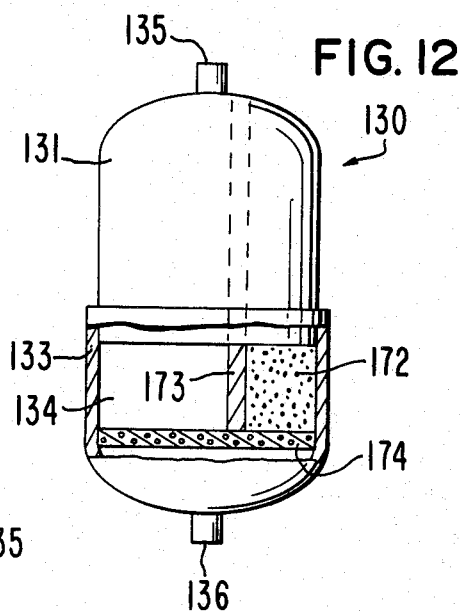
FIG. 12 is an opened view of an agent formulation chamber containing a beneficial agent, a release rate controlling film, and a filter; and, FIG. 13 is an opened view of a formulation chamber containing a beneficial agent in particle form, and a release rate controlling film.

FIG. 12 illustrates the formulation chamber containing drug 172 that is soluble in parenterally acceptable fluids that enter the formulation chamber, and in a presently preferred embodiment the formulation chamber houses a film 173 for controlling the rate of release of drug 172 in solution from the chamber. Film 173, in a preferred embodiment, is formed of a release rate controlling microporous polymer, such as a polycarbonate; or film 173 can be formed of a diffusional polymer such as ethylene-vinyl acetate copolymer, and the like. The chamber can also have a filter 174 of pore size of 0.1 micron to 5 micron, and more preferably 0.22 micron or 0.45 micron, for removing bacteria and unwanted matter from a flowing drug solution. The formulation chamber is illustrated in a film extended from the top of the formulation chamber to the bottom of the chamber with the drug placed on one side of the film. That is, the film can be placed vertically in the formulation chamber to the side of the inlet port confining the drug therein, with fluid passing through the film, forming a drug solution and then returning to the fluid passing through the formulation chamber for eventual administration to a patient.

Figure 13:
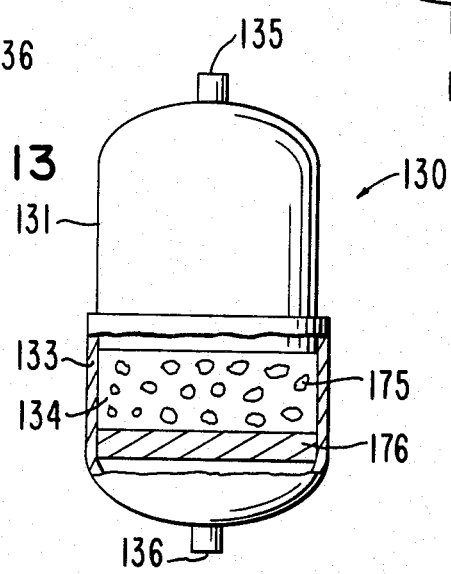

FIG. 13 illustrates the formulation chamber housing a multiplicity of agent particles 175 for forming an agent solution formulation with medical fluid that enters the chamber. The particles are supported by a membrane 176 that can be used to control the rate of agent formulation release from the formulation chamber.

The parenteral delivery system comprising the primary path and the secondary path with agent formulation chambers in each path can be used for administering many beneficial agents, especially where it is desirable to administer by infusion, and more particularly via the intravenous intra-arterial, intraperitoneal or subcutaneous routes. For example, the delivery system can be used in one presently preferred embodiment, in intravenous fluid replacement, such as administering plasma, or saline and simultaneously or intermittently administering a therapeutically effective amount of drug therewith; in another embodiment as a method in intravenous electrolyte-balance replacement, such as supplying sodium, potassium or chloride with drug(s) administered therewith to a patient in need of electrolyte restoration and an intravenous drug; and in a method of intravenous nutrition, such as supplying dextrose and concomitantly administering or periodically administering a parenterally administrable drug to a patient in need of such therapies.

The novel and useful invention provides a system and a method for obtaining the precise control of agent administration to a recipient. While there has been described and pointed out features of the invention as applied to presently preferred embodiments, those skilled in the art will appreciate that various modifications, changes, additions and omissions in the inventions illustrated and described can be made without departing from the spirit of the invention.

We claim:

1. A parenteral delivery system for administering a beneficial agent formulation to an animal, the system comprising:
   (a) a primary path for the flow of a parenterally acceptable fluid therethrough;
   (b) a formulation chamber in the primary path, the formulation chamber comprising:
      (1) a wall surrounding a lumen;
      (2) an inlet for letting fluid from the primary path into the formulation chamber;
      (3) a beneficial agent in the formulation chamber that forms an agent formulation with fluid that enters the formulation chamber;
      (4) a film extended from the top to the bottom of the formulation chamber in the formulation chamber; said film separating said agent from the flow path and comprising releasing means that aids in controlling the rate of release of beneficial agent from the formulation chamber;
      (5) an outlet for letting an agent formulation leave the formulation chamber;
   (c) a secondary path for the flow of a parenterally acceptable fluid therethrough;
   (d) a formulation chamber in the secondary path, the formulation chamber comprising:
      (1) a wall surrounding a lumen;
      (2) an inlet for letting fluid from the secondary path into the formulation chamber;
      (3) a beneficial agent in the formulation chamber that forms an agent formulation with fluid that enters the formulation chamber;
      (4) a film extended from the top to the bottom of the formulation chamber in the formulation chamber, said film separating said agent from the flow path and comprising releasing means that aids in controlling the rate of release of beneficial agent from the formulation chamber;
      (5) an outlet for letting an agent formulation leave the formulation chamber; and,
   (e) a common path in communication with the primary path and in communication with the secondary path for receiving agent formulation, which common path when the system is in use is in communication with the animal for administering beneficial agent formulation thereto.

2. The parenteral delivery system for administering the beneficial agent formulation according to claim 1, wherein the beneficial agent is placed to the side of the film.

3. The parenteral delivery system for administering the beneficial agent formulation according to claim 1, wherein the formulation chamber is in communication with a drip chamber.

4. A parenteral delivery system for administering a beneficial agent formulation to an animal, the system comprising:
   (a) a primary path for the flow of a parenterally acceptable fluid therethrough;
   (b) a formulation chamber in the primary path, the formulation chamber comprising:
      (1) a wall surrounding a lumen;
      (2) an inlet for letting fluid from the primary path into the formulation chamber;
      (3) about 5 milligrams to 20 grams of a solid beneficial agent in the formulation chamber that forms an agent formulation with fluid that enters the formulation chamber;

(4) a fluid permeable film in the formulation chamber to the side of the inlet that confines the beneficial agent therein, said film providing releasing means for said agent;

(5) an outlet for letting an agent formulation leave the formulation chamber;

(c) a secondary path for the flow of a parenterally acceptable fluid therethrough;

(d) a formulation chamber in the secondary path, the formulation chamber comprising:

(1) a wall surrounding a lumen;

(2) an inlet for letting fluid from the secondary path into the formulation chamber;

(3) about 5 milligrams to 20 grams of a solid beneficial agent in the formulation chamber that forms agent formulation with fluid that enters the formulation chamber;

(4) a fluid permeable film in the formulation chamber to the side of the inlet that confines the beneficial agent therein, said film providing releasing means for said agent;

(5) an outlet for letting an agent formulation leave the formulation chamber; and, (e) a common path in communication with the primary path and in communication with the secondary path for receiving agent formulation, which common path when the system is in use is in communication with the animal for administering beneficial agent formulation thereto.

5. The parenteral delivery system for administering the beneficial agent formulation according to claim 4, wherein the formulation chamber is in communication with a drip chamber.

6. An intravenous delivery system for administering a beneficial drug formulation to an animal, the system comprising:

(a) a primary path for the flow of an intravenously acceptable fluid therethrough;

(b) a formulation chamber in the primary path, the formulation comprising:

(1) a wall surrounding a lumen;

(2) an inlet for letting fluid from the primary path into the formulation chamber;

(3) about 5 milligrams to 20 grams of a solid, beneficial drug in the formulation chamber that forms a drug formulation with fluid that enters the formulation chamber;

(4) a film in the formulation chamber that aids in governing the rate of release of drug formulation from the formulation chamber, said film releasing the beneficial drug formulation by microporous, diffusion or osmotic physical chemical mechanisms.

(5) an outlet for letting an agent formulation leave the formulation chamber;

(c) a secondary path for the flow of an intravenously acceptable fluid therethrough;

(d) a formulation chamber in the secondary path, the formulation chamber comprising:

(1) a wall surrounding a lumen;

(2) an inlet for letting fluid from the secondary path into the formulation chamber;

(3) about 5 milligrams to 20 grams of a solid beneficial drug in the formulation chamber that forms a drug formulation with fluid that enters the formulation chamber;

(4) a film in the formulation chamber that aids in governing the rate of release of drug formulation from the formulation chamber, said film formed of a nontoxic material that releases the beneficial drug formulation by microporous, diffusion or osmotic physical-chemical mechanisms;

(5) an outlet for letting an agent formulation leave the formulation chamber; and, (e) a common path in communication with the primary path and in communication with the secondary path for receiving drug formulation, which common path when the system is in use is in communication with the animal for administering beneficial drug formulation thereto.

7. The intravenous delivery system for administering the beneficial drug formulation according to claim 6, wherein the formulation chamber is in communication with a drip chamber.

* * * * *